United States Patent [19]

Sturges

[11] Patent Number: 5,759,151

[45] Date of Patent: Jun. 2, 1998

[54] FLEXIBLE STEERABLE DEVICE FOR CONDUCTING EXPLORATORY PROCEDURES

[75] Inventor: Robert H. Sturges, Mt. Lebanon, Pa.

[73] Assignee: Carnegie Mellon University, Pittsburgh, Pa.

[21] Appl. No.: 486,758

[22] Filed: Jun. 7, 1995

[51] Int. Cl.$^6$ .................................................. A61B 1/00
[52] U.S. Cl. ............................................ 600/146; 600/139
[58] Field of Search ................................. 600/139–144, 600/146; 138/118, 118.1

[56] References Cited

U.S. PATENT DOCUMENTS

| | | | |
|---|---|---|---|
| 3,946,727 | 3/1976 | Okada et al. | 600/139 |
| 4,054,128 | 10/1977 | Seutert et al. | 600/141 X |
| 4,236,509 | 12/1980 | Takahashi et al. | 600/139 |
| 4,327,711 | 5/1982 | Takagi | 600/139 |
| 5,125,395 | 6/1992 | Adair | 600/144 X |
| 5,251,611 | 10/1993 | Zehel et al. | 128/4 |

OTHER PUBLICATIONS

IEE Conf. Proc. (1991).

*Primary Examiner*—Beverly M. Flannagan
*Attorney, Agent, or Firm*—Alan G. Towner; Walter J. Blenko, Jr.; Eckert Seamans Cherin & Mellott, LLC

[57] ABSTRACT

A flexible, steerable device for conducting exploratory procedures is disclosed. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath.

6 Claims, 5 Drawing Sheets

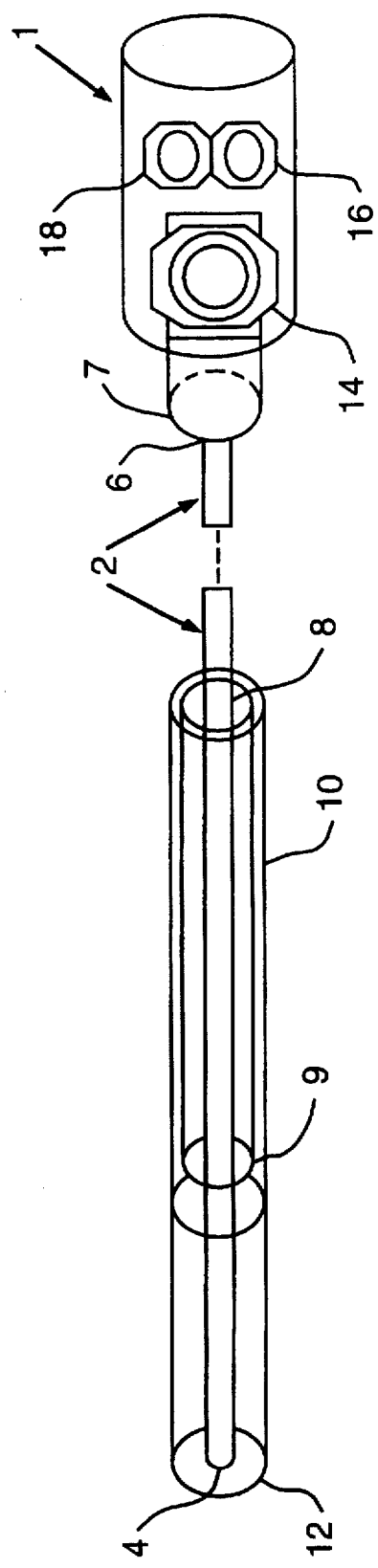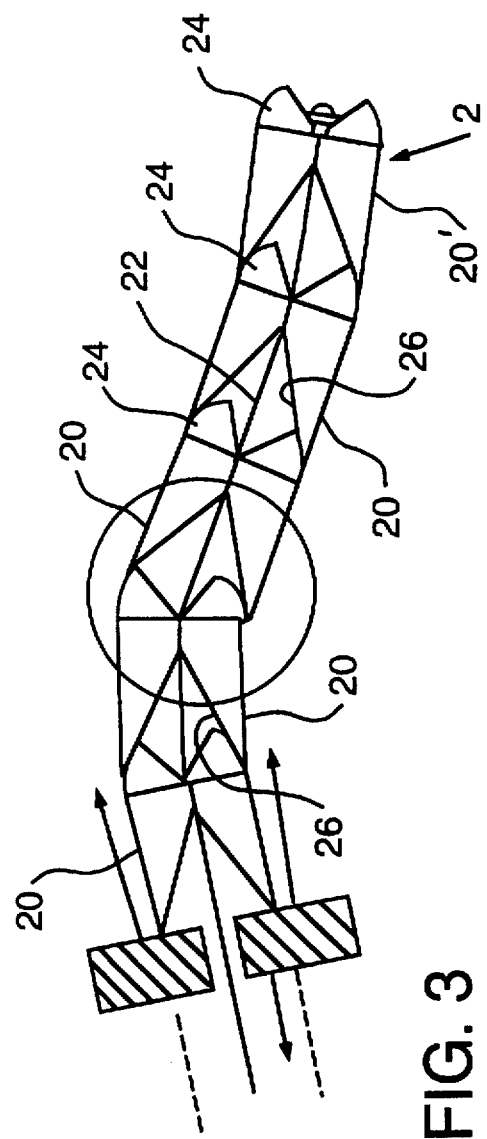
FIG. 1
FIG. 3

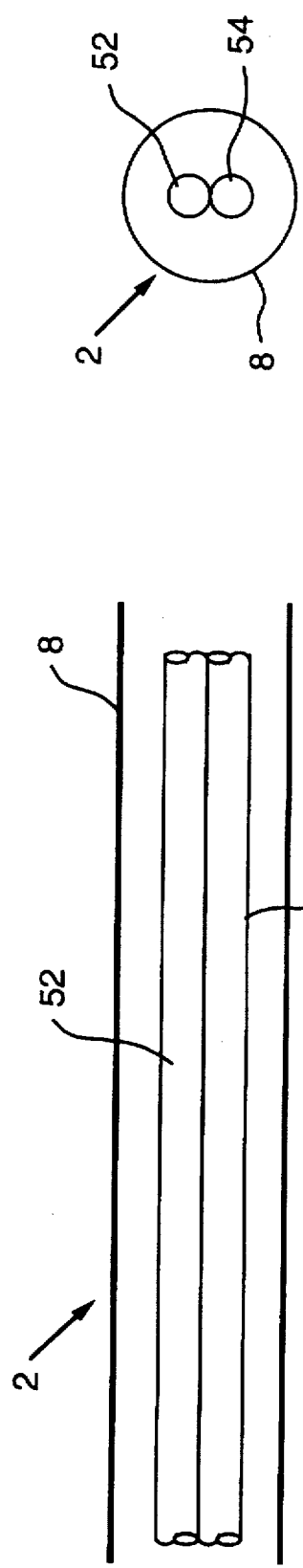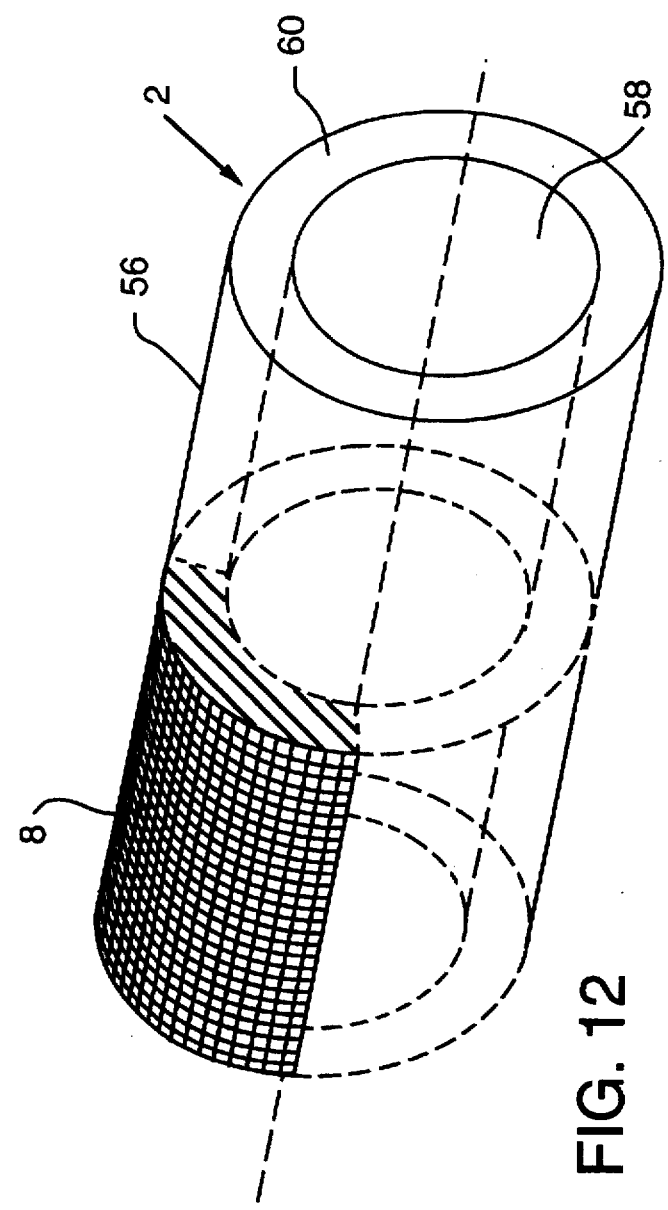

5,759,151

FLEXIBLE STEERABLE DEVICE FOR CONDUCTING EXPLORATORY PROCEDURES

BACKGROUND OF THE INVENTION

1. Field of the Invention

This invention relates to steerable devices for conducting exploratory procedures, and, more particularly, to such devices that may be used in confined conduits or in open space.

2. Background of the Invention

Instruments for visual diagnosis and therapy of the abdominal cavity, or "laparoscopes," typically employ a rigid tube or conduit that is inserted into the patient through a small incision. By rotating the tube about the point of entry into the body cavity, viewing devices, such as fiber optics or miniature television, may be pointed toward points of interest. The forward motion of the laparoscope can be approximately directed as the instrument is pushed into space formed by insufflation of the abdomen.

Smaller rigid borescopes are similarly employed in neurosurgery. The borescope is inserted into the cranial cavity of the patient through a small hole drilled on the skull.

Instruments for examination and therapy of the esophagus and colon, or "endoscopes," typically employ a passage in a flexible hose or conduit which is inserted into the patient from the mouth or anus. The distal end of the endoscope may be steered or pointed by the endoscopist by means of manual controls means on the proximal end of the instrument. Typically, the first few inches of the distal end of the instrument may be flexed 90 or more degrees in any direction with respect to the longitudinal axis of the body of the endoscope by pulling on one or more of four steering cables, or tendons, extending along the length of the instrument. Viewing devices may be directed toward points of interest, and the forward motion of the endoscope may be approximately directed as the instrument is pushed into the gut. In addition, a trained endoscopist can employ the flexed distal end of the instrument to temporarily distort the natural curve of the gut by hooking the instrument over a curve in the gut wall and pulling on the instrument. That maneuver is typically used in colonoscopy to straighten the gut somewhat to facilitate further insertion of the instrument.

Laparoscopes offer limited access to internal organs. Due to their rigid design, they must access portions of the cavity in generally straight lines form the point of entry. Similarly, borescopes must enter the skull from a single point in the skull and be moved in a generally straight line to their point of use, sometimes requiring that the instrument pass through other tissues.

Endoscopes apply pressure to the walls of the gut as they are inserted, especially after the instrument has been inserted to lengths of 50 cm or more. At such insertion lengths, the instrument will typically be following at least one relatively sharp curve around an angle of at least 90 degrees. Under those conditions, any forward or backward motion of the instrument will necessarily cause pressure to be exerted on the gut walls ar the curves. That problem is compounded because instruments must be stiff enough to avoid buckling when inserted against resistive forces generated by the gut. The gut often reacts to the presence of an endoscope by contracting radially, thereby constricting its passage. Attempts at forward or backward movement of the endoscope under those conditions may result in relatively large and potentially dangerous forces being applied to the walls of the gut at points of contact with the instrument. It has been noted that the best endoscopists cannot always reach the cecum (the end of the large intestine at the appendix) because of cramping of the gut, the inability to control the position of the endoscope along its entire length, and the danger of applying forces which might herniate or rupture the gut.

SUMMARY OF THE INVENTION

This invention provides a flexible, steerable device that may be controlled to maneuver in curved paths through confined spaces without damaging nearby tissue. The device may be used as a laparoscope, a borescope or an endoscope. The device also provides a relatively stable platform for the deployment of medical devices through the distal end of the instrument which remains relatively motionless in response to motions of the gut as a whole. The device may also be used for non-medical applications.

The flexible steerable device of this invention includes at least one spine having a distal end and a proximal end. The spine includes stiffening means to selectively render portions of the spine rigid and flexible along its length. A flexible sheath surrounds each spine. The sheaths also have proximal and distal ends. The spine and the sheath are axially slidably moveable relative of one another so that the sheath will follow the shape of the spine when the spine is in the stiffened state and resist further flexure when the spine is in the flexible state. A steerable distal tip is mounted on the distal end of the sheath. The distal tip is in communication with control means mounted on the proximal end of the spine for steering the distal tip. Means are mounted on the distal end of the device for selectively activating and deactivating the stiffening means of the spine. At least one of the flexible sheaths may be secured to a flexible instrument conduit that extends generally axially parallel with the sheath and spine. The instrument conduit carries visual and/or therapeutic medical instruments.

In one embodiment, each spine includes a series of generally hollow segments having a cable extending axially therethrough. The distal end of the cable is secured to the distal-most segment. The stiffening means includes a mechanism of tensioning and relaxing the cable. Tensioning the cable compresses the series of segments against on another and creates a mechanical fit between adjacent segments. The mechanical fitting together of the segments renders the series of segments rigid without altering the configuration of the series of segments and without altering the length of the cable. Relaxing the cable renders the series of segments flexible.

Other advantages, features and objects of this invention will become apparent from the following description of present preferred embodiments on reference to the appended drawings.

BRIEF DESCRIPTION OF THE DRAWINGS

FIG. 1 is a partial cut-away view of an embodiment of this invention.

FIG. 3 is a longitudinal sectional view of the spine of the embodiment of FIG. 1.

FIG. 10 is a longitudinal sectional view of a portion of one embodiment of the spine of this invention.

FIG. 11 is a cross-sectional view of the embodiment shown in FIG. 10, taken through line 11—11 of FIG. 10.

FIG. 12 is a partial perspective view of another embodiment of the spine of this invention.

DETAILED DESCRIPTION OF PREFERRED EMBODIMENTS

Figure 2:
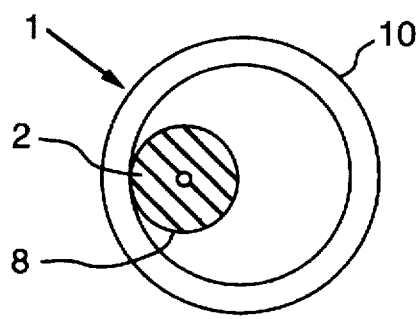
FIG. 2 is a cross-sectional view of the embodiment of FIG. 1.

FIGS. 1 and 2 show a flexible steerable device 1 of this invention. The device 1 includes a spine 2 having a distal end 4 and a proximal end 6. Spine 2 includes stiffening means for selectively rendering portions of spine 2 rigid and flexible along its length, as will be more fully described as follows. Spine 2 extends through and is generally coaxial with a flexible sheath 8. Sheath 8 has a proximal end 9 and a distal end 9 and preferably extends along the entire length of spine 2. Sheath 8 may be made from polyurethane, polyvinyl chloride, or any other suitable elastic polymer. Sheath 8 and spine 2 are slidably movable with respect to one another. The clearance between spine 2 and sheath 8 is such that the components may easily move relative to one another and to resist buckling. Sheath 8 is secured to a flexible instrument conduit 10 having a proximal end and 9 distal end 9. Instrument conduit 10 is preferably of a diameter so that it may be inserted into a human gut and may be used to carry medical instruments, such as visual devices, illuminating devices, surgical devices and the like. It will be appreciated, however, that this invention may be used with a conduit of virtually any size, depending on the stiffness of the various components and the operating environment. Instrument conduit 10 may be made from braided stainless steel wire, spiral formed metal, plastic conduit or any other suitable material. Steerable distal tip may be mounted on the distal end of sheath 8. Steerable tip 12 is in communication with steering controller 14 mounted on the proximal end of device 1. Distal tip 12 and controller 14 are of types known to those skilled in the art. The distal end 4 of the spine 2 has a maximum limit of travel wherein the distal end 4 is inserted into the steerable tip 12, as shown in FIG. 1. The distal end 4 of the spine 2 has a minimum limit of travel wherein the distal end 4 is retracted from the steerable tip 12 into the conduit 10.

A spine stiffening/relaxing controller 16 and a spine advance/retract controller 18 are also mounted on the proximal end of device 1. Controllers 16, 18 may be types known to those skilled in the art, such as manually operated, servo motor driven, mechanically driven, pneumatic powered, hydraulic powered, electrical, thermal or any other suitable types of controllers.

FIG. 3 illustrates a preferred embodiment of the spine 2 of this invention. Spine 2 includes a plurality of generally cylindrical segments 20 strung on a flexible cable 22. The distal-most segment 20' is secured to cable 22. The proximal-most segment is attached to the proximal end of the device 1 and is supported with respect to the ground. The proximal end of cable 22 is operatively connected to spine stiffening/relaxing controller 16. The intervening segments are free to slide axially on cable 22 and move radially at each end. When cable 22 is relaxed, the segments are free to move such that the spine 2 is flexible.

Each segment 20 includes a rounded distal end 24 and an open proximal end 26. The ends 24 and 26 of each segment 20 are structured such that the open proximal end 26 of each segment receives the rounded distal end 24 of the immediately proximately adjacent segment 20 therein. The segments are oriented into a desired configuration, such as following the curve of a patient's gut and the cable 22 is tensioned. When cable 22 is tensioned, the segments are pulled together and the frictional forces of the mechanical fit between the segments to hold the segments 20 in place in the previously established orientation, thereby causing the spine to stiffen in that preestablished position.

In this embodiment, the opening of each open proximal end 26 of each segment 20 extends into the body of each segment 20 is generally cone shaped. The conical shape of the openings enables the segments to maintain their radial orientation with respect to one another without substantially lengthening or shortening of cable 22. If cable 22 were to shorten when tensioned, it would cause the segments to move from their previously established position (corresponding to shape of the patient's gut) and become realigned. The realignment of the segments of the stiffened spine could apply undesired pressure on the walls of the patient's gut.

Segments 20 may be made from hardened stainless steel, hardened 7075 aluminum alloy or any other suitable material. About three to four segments 20 are used per inch of length of spine 2. The length of each segment 20 is preferably about ⅓ inch and the outside diameter of each segment 20 is about ¼ inch. It has been found that those dimensions and number of segments 20 provide suitable flexibility without compromising stiffness.

Figure 4:
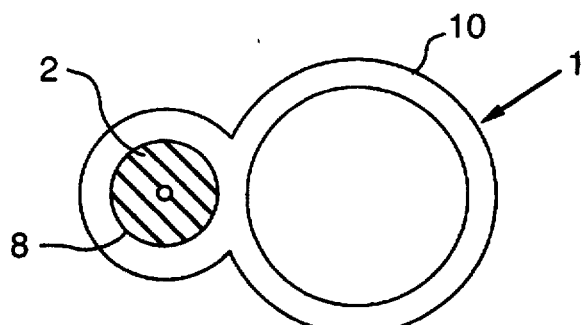
FIG. 4 is a cross-sectional view of another embodiment of this invention.

FIG. 4 shows a cross sectional view of an alternative embodiment of the device 1 of FIG. 1. The devices of FIGS. 1 and 2, and 4 each have a single spine 2 and are particularly suitable for use as endoscopes that are inserted into conduits within a patient's body.

The operation of the device of FIGS. 1–4 as used as an endoscope is as follows, by way of example:

1. Spine 2 is retracted to its minimum limit and made rigid. The distal end of device 1 (sheath 8 and instrument conduit 10) is inserted into the gut up to the first substantial curve of the gut.

2. Distal tip 12 is flexed to observe and determine the next desired direction of forward travel. Spine 2 is relaxed and advanced to its maximum limit and stiffened. Distal tip 12, sheath 8 and instrument conduit 10 remain stationary with respect to the patient during the advancing of spine 2.

3. Distal tip 12, sheath 8 and instrument conduit 10 are inserted farther into the gut using rigid spine 2 as a guide. Spine 2 remains relatively stationary with respect to the patient as distal tip 12, sheath 8 and instrument conduit 10 are further inserted into the gut. The total forward movement of the device should equal the travel limit of spine 2 within sheath 8. Steering control of distal tip 12 should preclude buckling or undesired bending of the short portion of the sheath not supported by rigid spine 2.

4. Steps 2 and 3 are repeated cyclically until distal tip 12 reaches the target site in the gut. Spine 2 is advanced to the extent of distal tip 12 and made rigid.

When spine 2 is relaxed, the device assumes the natural shape of the gut and does not place undesired pressure thereon. It will be appreciated that an endoscope of this invention will be considerably more flexible than currently used endoscopes. An endoscope of this invention would be so flexible and susceptible to buckling upon insertion into the gut so as to be inoperable without the use of spine 2.

It will also be appreciated that when the distal tip 12 is in position at the target site spine 2 will positionally support distal tip 12 to provide a stable platform for using medical instruments.

The following is an alternative example of the operation of an endoscope of this invention:

1. Spine 20 is advanced to its maximum limit and made rigid. The distal end of device 1 is inserted into the gut to the first substantial curve.
2. Sheath 10, distal tip 12 and instrument conduit 10 are advanced into the gut over the spine. During this operation, spine 2 is generally stationary with respect to the gut.
3. Spine 20 is relaxed and advanced to its maximum length. Distal tip 12 is flexed to determine the desired direction of travel and spine 20 is stiffened in the new position.

This cycle is repeated until distal tip 12 is reaches the target site.

Removal of a conventional endoscope may exert undesired pressure on the gut, especially when the gut has cramped after insertion of the endoscope. With this invention, spine 2 may be used as a guide to withdraw the conduit without causing undue stress. The following steps describe one operation for removal of an endoscope of this invention:

1. Spine 2 is relaxed and retracted to its minimum axial travel limit.
2. Spine 2 is stiffened, thereby taking the shape of the gut through which it extends. Sheath 8, instrument conduit 10 and distal tip 12 are withdrawn from the gut as spine 2 is extended the its maximum axial travel limit such that spine 2 remains relatively stationary with respect to the gut.

Figure 5:
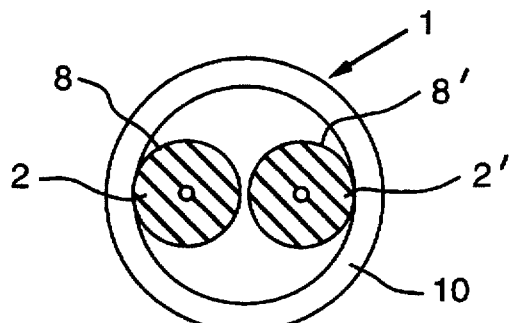
FIG. 5 is a cross-sectional view of another embodiment of this invention.
Figure 6:
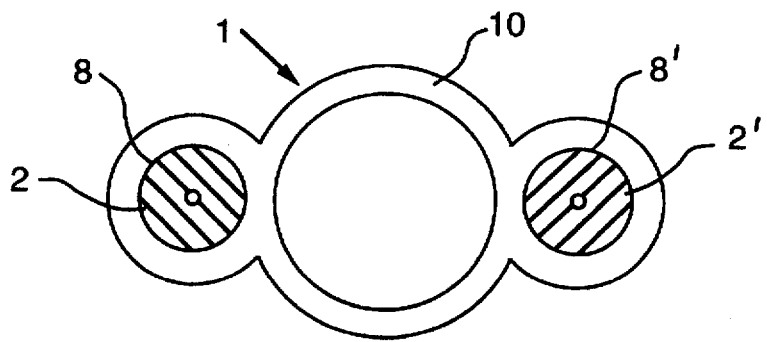
FIG. 6 is a cross-sectional view of another embodiment of this invention.

FIGS. 5 and 6 show cross-sectional views of alternative embodiments of this invention having two independently operable spines 2, 2' and two sheaths 8, 8'. Sheaths 8, 8' are secured to an instrument conduit 10. These embodiments are particularly useful as laparoscopes or borescopes.

An example of the operation of the embodiments of FIGS. 5 and 6 is as follows:

1. Each spine 2, 2' is retracted to its minimum axial limit and made rigid. The distal tip 12, instrument conduit 10 and sheaths 8, 8' are inserted into the body and advanced up to the first obstruction.
2. Distal tip 12 is flexed to observe and determine the next desired direction of forward travel. Once that direction has been determined, one of spines 2, is relaxed. The relaxed spine is advanced to its maximum axial limit and stiffened.
3. The second spine 2' is relaxed and advanced to its maximum axial limit. Spine 2' is then stiffened. (This step is repeated for any additional spines not yet advanced.)
4. Sheaths 8, 8', distal tip 12 and instrument conduit 10 are advanced farther into the patient using the stiffened spines 2, 2' as guides. Simultaneously as the device is advanced, spines 2, 2' are retracted to their minimum axial limit so that spines 2, 2' remain relatively stationary with respect to the patient. The distance the device is inserted during this step should be equal to the travel limit of spines 2, 2'. Controlling distal tip 12 resists buckling of the portion of the device not supported by spines 2, 2' as the device is advanced.

The cycle is then repeated until the target site is reached.

The advance of a relaxed spine into the portion of a sheath the shape of which is controlled by the flexure of distal tip 12 has the effect of reproducing that shape when the spine is made rigid. As long as one spine remains rigid in that area, the entire history of the flexures of distal tip 12 will be recorded in the shape of the rigid spine.

Figure 7:
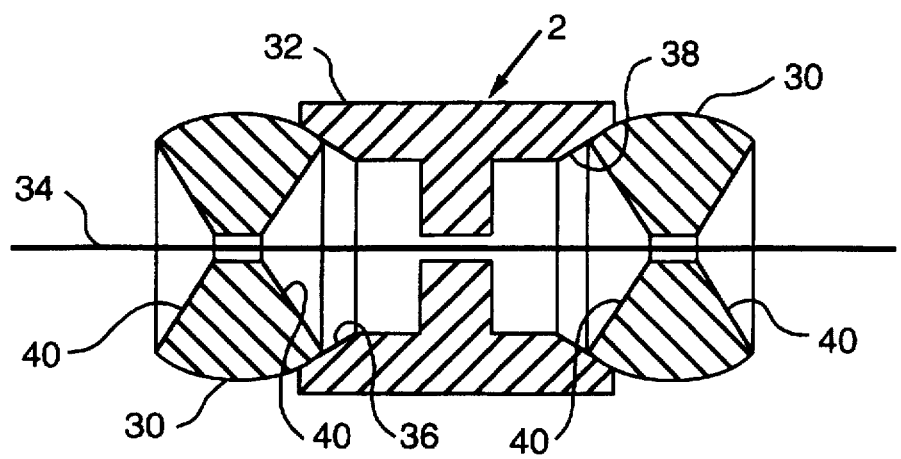
FIG. 7 is a longitudinal sectional view of a portion of one embodiment of the spine of this invention.

FIG. 7 shows another embodiment of a portion of a spine 2 of this invention. This embodiment consists of an alternating series of generally spherical beads 30 and generally cylindrical beads 32 strung on a flexible cable 34. The ends 36, 38 of cylindrical beads 32 are structured to receive the adjacent spherical bead 30 therein in a mechanical fit by tensioning cable 34. When cable 34 is relaxed, the beads 30, 32 are free to move so that the relaxed spine may acquire the shape of the curve of the gut, or the like. When cable 34 is tensioned, the beads 30, 32 are forced together and the spine 2 becomes rigid. The truncated conical shape of the openings 36, 38 in cooperation with the spherical shape of beads 30 enable spine 2 to maintain the shape it attained while flexible after it is made rigid. The conical openings 40 in spherical beads 30 permit radial movement of the beads without requiring that the length of cable 34 be altered when the spine 2 goes from the flexible state to the rigid state.

Spherical beads 30 are preferably made of ceramic material and cylindrical beads 32 are preferably made of aluminum. It will be appreciated, however, that any suitable material may be used. Preferably, each spherical bead 30 has an outside diameter of about ¼ inch. Each cylindrical bead has a length and outside diameter both equal to about ¼ inch.

Figure 8:
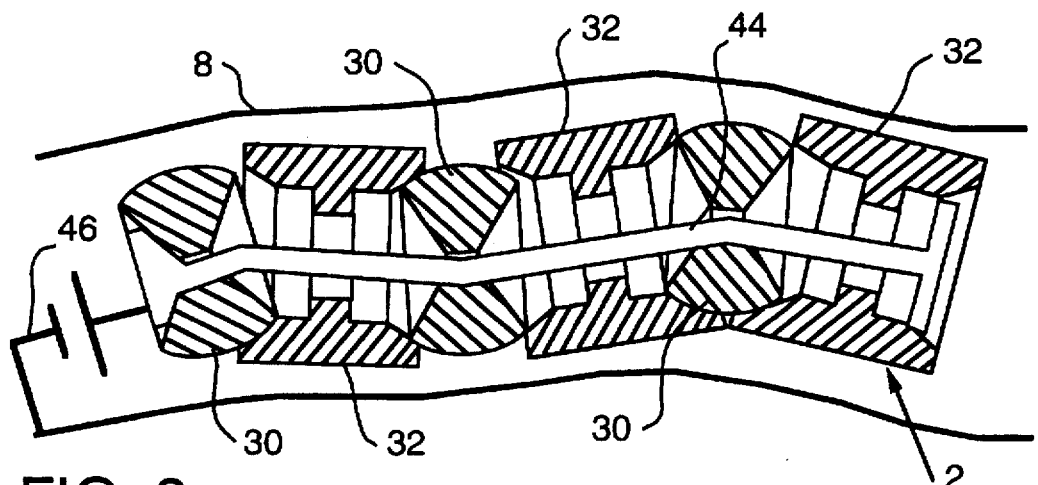
FIG. 8 is a longitudinal sectional view of a portion of one embodiment of the spine of this invention.

FIG. 8 shows an embodiment of this invention wherein the spine 2 is made rigid by the application of electrical current to one or more electrical cable segments 44. Beads 30, 32 are threaded onto an electrical cable that has been preloaded in tension. Accordingly, the beads 30, 32 are compressed together rendering spine 2 rigid under normal conditions. Electrical current is applied to electrical cable 44 from a power source 46. The applied current causes the electrical cable 44 to expand and lengthen, thereby rendering spine 2 flexible. Removal of the current permits cable to return to its original length, again rendering the spine 2 rigid. Electrical cable 44 preferably is made from a material that has a relatively high coefficient of thermal expansion to achieve the desired amount of lengthening from the application of current. It will be appreciated that an electrical cable 44 may also be used with a spine made up of segments of the type shown in FIG. 3.

Figure 9:
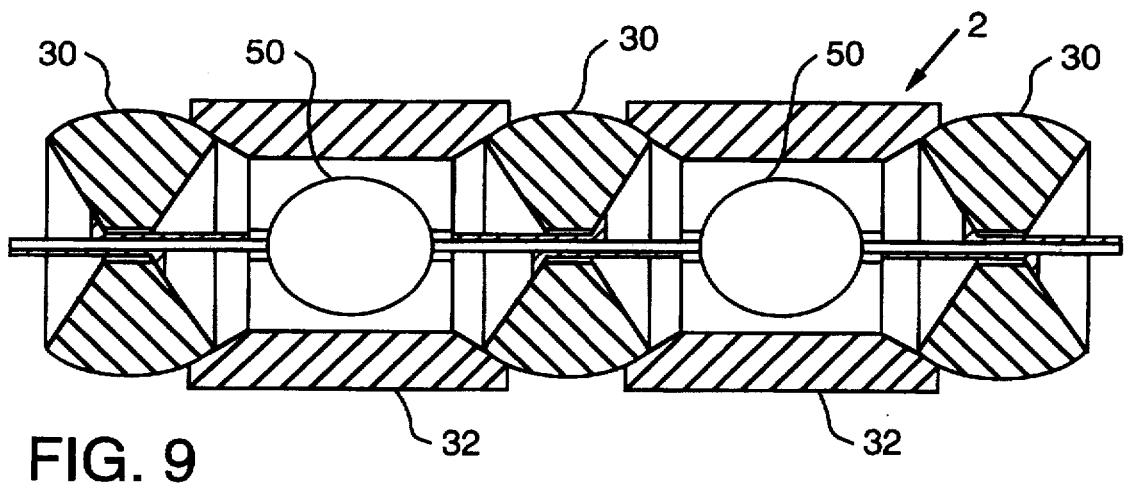
FIG. 9 is a longitudinal sectional view of a portion of one embodiment of the spine of this invention.

FIG. 9 shows another embodiment of a spine 2 of this invention. In this embodiment, the force required to draw the beads 30, 32 together to render the spine 2 rigid is generated by the application of fluid pressure to a fluid powered elastic actuator 50 positioned in each cylindrical bead 32. Each actuator is connected to the adjacent cylindrical beads 30. Actuators 50 are preferably prolate spheroids which inflate upon the application of fluid pressure. As the actuators inflate, their ends are forced inward, thereby drawing the beads 30, 32 into forceful contact with one another, rendering the spine 2 rigid. This embodiment may also be used with the segments of the embodiment of FIG. 3.

FIGS. 10 and 11 show another embodiment of the spine 2 of this invention. Spine 2 consists of a pair of flexible conduits 52, 54. Conduit 52 is filled with a fusible material that is molten at body temperature, such as gallium. Conduit 54 provides a passage for a heat exchange fluid, such as chilled water. Conduits 52, 54 are in thermal contact with one another. Passing of a cold fluid through conduit 54 freezes the fluid in conduit 52, rendering spine 2 rigid. Passing a warm fluid through conduit 54 melts the fluid in conduit 52, rendering spine 2 flexible. In the event of a failure of conduit 54 to supply the heated fluid to render the spine 2 flexible, the fluid in conduit 52 will eventually melt as it returns to body temperature, thereby permitting removal of the device from the patient.

FIG. 12 shows yet another embodiment of the spine 2 of this invention. This embodiment is substantially similar to the embodiment shown in FIGS. 9 and 10, except that only one conduit 56 is provided. Conduit 56 includes a heat exchange fluid tube 58 surrounded by a braided tube 60 filled with the fusible material. Tubes 58 and 60 are arranged coaxially.

Figure 13:
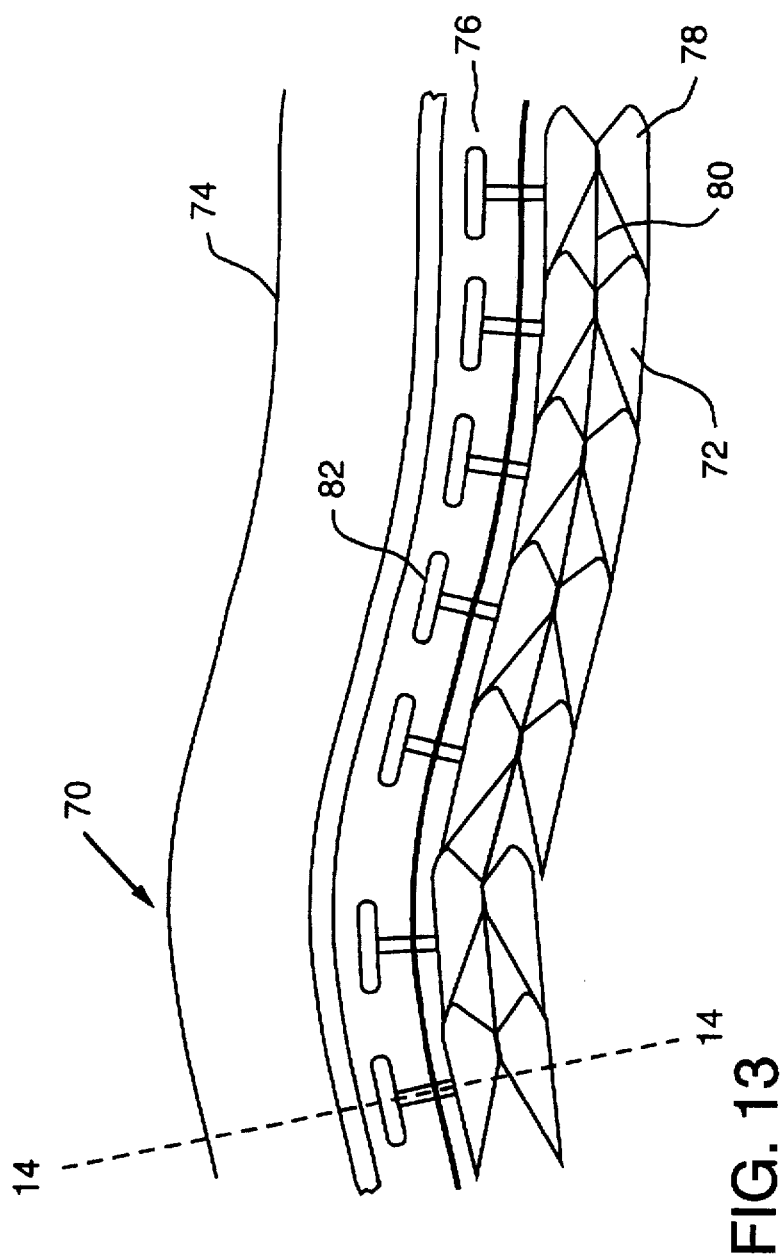
FIG. 13 is a longitudinal sectional view of a portion of another embodiment of this invention.
Figure 14:
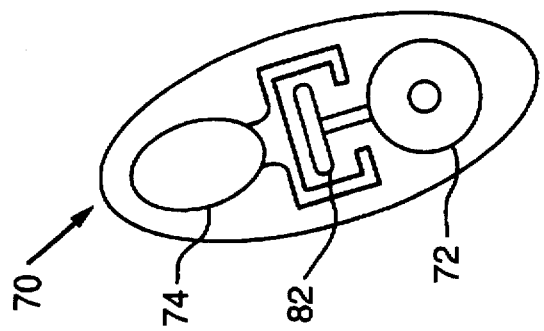
FIG. 14 is a cross-sectional view of the embodiment shown in FIG. 13, taken through line 14-14 of FIG. 13.

Thus far this invention has been described in terms of applications in medical devices. It will be appreciated, however, that the invention may be utilized in other applications as well. For example, the invention could be used to control manipulators working in crowded environments. The manipulator may be navigated, either manually or by robotic control, through the crowded environment in the manners described above. In these types of applications, the mechanisms for stiffening the spines could be more robust than those described above, thereby permitting the use of greater forces and speeds. FIGS. 13 and 14 show an embodiment of this invention that may be adapted for use with higher forces. The device 70 includes a spine 72, a conduit 74 and an articulated track 76 mounted along the axial extent of conduit 74. Spine 72 is made of a plurality of segments 78 strung on a flexible cable 80. Segments 78 have generally the same configuration as those of FIG. 3, discussed above, except that segments 78 may be significantly larger in size. In addition, each segment 78 is provided with a guide roller 82 extending outwardly therefrom. Guide rollers 82 fit into track 76, thereby enabling track 76 to function in the same manner as the sheath discussed above. The means for controlling the advancing and retracting movement of the device and for rendering spine 72 rigid an flexible are of a type known to those skilled in the art, such as mechanical, electrical, hydraulic or pneumatic.

Many other variations and other embodiments of this invention would be possible without departing from the scope of the following claims.

What is claimed is:

1. A flexible steerable device comprising:

at least one spine having a distal end and a proximal end, said spine having stiffening means in operative connection therewith to selectively render portions of said spine rigid and flexible along its length;

a flexible sheath surrounding said spine;

a flexible instrument conduit secured to said flexible sheath, said spine being axially slidably moveable relative to said sheath and said instrument conduit whereby said sheath and said instrument conduit will follow the shape of said spine when said spine is in a stiff state and resist further flexure when said spine is in a flexible state;

a steerable distal tip in communication with said distal end of said spine, wherein said distal end of said spine is insertable into and retraceable from said steerable distal tip, said steerable distal tip being in communication with control means mounted on said proximal end of said spine for steering said distal tip; and means for selectively activating and deactivating said stiffening means at said proximal end of said spine.

2. The flexible steerable device of claim 1, wherein each said spine includes a series of generally hollow segments having a cable extending axially therethrough and secured to the distal-most segment; and said stiffening means includes means for selectively tensioning and relaxing said cable whereby tensioning said cable compresses said series of segments and creates a mechanical fit between adjacent segments thereby making said series of segments rigid without altering the configuration of said series of segments and without altering the length of said cable.

3. The flexible steerable device of claim 2, wherein each said segment having a rounded distal portion and a generally cylindrical portion having an open proximal end, said open proximal end being structured to receive a portion of the rounded distal portion of the immediately proximally adjacent segment therein.

4. The flexible steerable device of claim 2, wherein said spine includes an alternating series of rounded beads and open ended cylinders having a cable extending therethrough, said open ends of said cylinders being structured to receive with friction fit a portion of a bead that is adjacent thereto along said cable when said cable is tensioned.

5. The flexible steerable device of claim 1, wherein said flexible sheath is secured to an instrument conduit that extends generally axially parallel with said sheath and said spine.

6. The flexible steerable device of claim 2, wherein at least two said spines are provided, each said spine being independently operable from the other; and one of said flexible sheaths surround each said spine.

* * * * *

UNITED STATES PATENT AND TRADEMARK OFFICE
CERTIFICATE OF CORRECTION

PATENT NO. : 5,759,151
DATED : June 2, 1998
INVENTOR(S) : Robert H. Sturges It is certified that error appears in the above-identified patent and that said Letters Patent is hereby corrected as shown below:

```
Column 3, line 38, before "distal" insert -- and a --.

Column 6, line 62, change "50" to -- 50 --.

Column 7, line 12, change "flexible,the" to -- flexible, the--.

Column 7, line 45, change "an" to -- and --.
```

Signed and Sealed this

Twenty-eighth Day of September, 1999

*Attest:*

Q. TODD DICKINSON

*Attesting Officer*   *Acting Commissioner of Patents and Trademarks*